United States Patent
Kappler et al.

US008246951B2

(10) Patent No.: US 8,246,951 B2
(45) Date of Patent: *Aug. 21, 2012

(54) COLLAGENOLYTIC ACTIVE ENZYME CONTAINING COMPOSITIONS, AND THEIR USE IN THE DENTAL FIELD

(75) Inventors: Oliver Kappler, Weilheim (DE); Ingo R. Haeberlein, Weilheim (DE)

(73) Assignee: 3M Deutschland GmbH, Neuss (DE)

( * ) Notice: Subject to any disclaimer, the term of this patent is extended or adjusted under 35 U.S.C. 154(b) by 984 days.

This patent is subject to a terminal disclaimer.

(21) Appl. No.: 12/132,315

(22) Filed: Jun. 3, 2008

(65) Prior Publication Data

US 2009/0117092 A1    May 7, 2009

Related U.S. Application Data

(62) Division of application No. 11/128,553, filed on May 13, 2005, now abandoned.

(30) Foreign Application Priority Data

May 24, 2004 (EP) .................................... 04012256

(51) Int. Cl.
*A61K 38/48* (2006.01)
(52) U.S. Cl. ...... 424/94.63; 424/85.1; 424/50; 424/94.2
(58) Field of Classification Search ................ 424/94.63
See application file for complete search history.

(56) References Cited

U.S. PATENT DOCUMENTS

| | | | |
|---|---|---|---|
| 4,355,022 A | 10/1982 | Rabussay | |
| 4,364,926 A | 12/1982 | Yokogawa et al. | |
| 4,693,888 A | 9/1987 | Miyahara et al. | |
| 4,732,758 A | 3/1988 | Hurion et al. | |
| 5,286,405 A | 2/1994 | Rennie | |
| 5,386,024 A | 1/1995 | Kacian et al. | |
| 5,439,935 A | 8/1995 | Rawlings et al. | |
| 5,670,132 A | 9/1997 | Griffiths et al. | |
| 6,090,381 A | 7/2000 | Leung et al. | |
| 6,105,761 A | 8/2000 | Peuker et al. | |
| 6,254,856 B1 | 7/2001 | Tsuchiya | |
| 6,287,550 B1 | 9/2001 | Trinh et al. | |
| 6,465,236 B1 | 10/2002 | Nishino et al. | |
| 6,521,215 B2 | 2/2003 | Okay | |
| 6,610,475 B1 | 8/2003 | Kacian et al. | |
| 6,752,989 B1 | 6/2004 | Haberlein et al. | |
| 7,097,075 B2 | 8/2006 | Peuker et al. | |
| 2002/0028251 A1 | 3/2002 | Okay | |
| 2003/0211054 A1 | 11/2003 | Szeles et al. | |
| 2004/0029171 A1 | 2/2004 | Wagner et al. | |
| 2004/0065679 A1 | 4/2004 | Peuker et al. | |
| 2004/0071636 A1 | 4/2004 | Delisle | |
| 2004/0120901 A1 | 6/2004 | Wu et al. | |
| 2005/0265932 A1 | 12/2005 | Kappler et al. | |
| 2006/0115436 A1 | 6/2006 | Haberlein et al. | |
| 2008/0213196 A1 | 9/2008 | Haberlein et al. | |
| 2008/0241122 A1 | 10/2008 | Kappler | |
| 2009/0117092 A1 | 5/2009 | Kappler et al. | |

FOREIGN PATENT DOCUMENTS

| | | |
|---|---|---|
| CN | 1216463 | 5/1999 |
| DE | 1 944 308 | 3/1971 |
| DE | 100 56 212 | 5/2002 |
| DE | 10237317 | 3/2004 |
| EP | 0 824 910 | 2/1998 |
| EP | 0 884 950 | 12/1998 |
| FR | 2 651 433 | 3/1991 |
| GB | 1033229 | 6/1966 |
| GB | 1265468 | 3/1972 |
| JP | S48-034897 B | 10/1973 |
| JP | 57 142910 A | 3/1982 |
| JP | S58-148828 A | 9/1983 |
| JP | H07-069854 | 3/1995 |
| JP | H07-157419 | 6/1995 |
| JP | H11-502527 | 3/1999 |
| JP | 2001-509535 | 7/2001 |
| JP | 2001-513139 | 8/2001 |
| JP | 2002078489 A | 3/2002 |
| WO | WO 92/10165 | 6/1992 |
| WO | WO 96/07329 | 3/1996 |
| WO | WO 97/08669 | 3/1997 |
| WO | WO 97/38669 | 10/1997 |
| WO | WO 98/20838 | 5/1998 |
| WO | WO 98/26807 | 6/1998 |
| WO | WO 00/27204 | 5/2000 |
| WO | WO 01/37787 A1 | 5/2001 |
| WO | WO 02/06820 | 1/2002 |
| WO | WO 02/38468 | 5/2002 |
| WO | WO 04/000222 | 12/2003 |
| WO | WO 2004/017988 | 3/2004 |
| WO | WO 2004/047782 | 6/2004 |
| WO | WO 2004/060325 A1 | 7/2004 |

OTHER PUBLICATIONS

Elkholany et al., Chemo-mechanical method: A valuable alternative for caries removal, Dental News, vol. xi, 2004, p. 16-22.*
Hoffmann-Axthelm, Lexikon der Zahnmedizin, Berlin, Germany 1995, 6.(11.) edition, cover page, title page, and pp. 372-375, 582-585, 808-809.
Harrington et al., Bacterial Collagenases and Collagen-Degrading Enzymes and Their potential Role in Human Disease, Infect. Immun., Jun. 1996, 64(6): 1885-1891.
Lide, Laboratory Solvents and Other Liquid Reagents, CRC Handbook of Chemistry and Physics, 87$^{th}$ Ed. Boca Raton, RL 2006-2007, pp. 15-13 to 15-22.

(Continued)

*Primary Examiner* — Michael G Wityshyn
*Assistant Examiner* — Tiffany Gough
(74) *Attorney, Agent, or Firm* — Nicole J. Einerson

(57) ABSTRACT

The invention relates to a composition comprising at least one collagenolytic active enzyme with enzymatic activity at acidic pH for drilless enzymatic caries removal. Furthermore, the present invention relates to a process of producing this collagenolytic active enzyme comprising composition and to processes of removing caries. The invention also relates to the use of collagenolytic active enzyme comprising compositions for producing a treatment agent for dental applications.

19 Claims, No Drawings

OTHER PUBLICATIONS

Optim Glycerine Viscosity datasheet [online] Dow Chemical Company, Midland, MI, 1995-2007 [retrieved on Oct. 23, 2007] Retrieved from the Internet: URL:http://www.dow.com/glycerine/resources/table18.htm; 2pgs.

Oyama et al., "A CLN2-Related and Thermostable Serine-Carboxyl Proteinase, Kumamolysin: Cloning, Expression, and Identification of Catalytic Serine Residue," J. Biochem. vol. 131, No. 5, pp. 757-765 (2002).

Comellas-Bigler et al., "The 1.4 Å Crystal Structure of Kumamolysin: A Thermostable Serine-Carboxyl-Type Proteinase," Structure, vol. 10, pp. 865-876, Jun. 2002.

Tsuruoka et al., "Collagenolytic Serine-Carboxyl Proteinase from *Alicyclobacillus sendaiensis* Strain NTAP-1: Purification, Characterization, Gene Cloning, and Heterologous Expression," Applied and Environmental Microbiology, vol. 69, No. 1, Jan. 2003, pp. 162-169.

Wlodawer et al., "Structural and enzymatic properties of the sedolisin family of serine-carboxyl peptidases," Acta Biochimica Polonica, vol. 50, No. Jan. 2003, pp. 81-102.

Kidd et al., "The use of a caries detector dye during cavity preparation: a microbiological assessment," (1993), Br. Dent. J. 174: pp. 245-248.

Perdigao et al., "Field emission SEM comparison of four postfixation drying techniques for human dentin," (1995) J Biomed Mat Res 29: pp. 1111-1120.

Banergee et al., "In vitro Evaluation of Five Alternative Methods of Carious Dentine Excavation," Caries Res., 2000, 34: pp. 144-150.

Brännström et al., "Invasion of Microorganisms and Some Structural Changes in Incipient Enamel Caries", (1980), *Caries Res.*, 14: 276-284.

Endodontie, Heinemann (ed.), Urban & Fischer (2001), p. 82, p. 89.

Kidd et al., Edited by Fejerskov & Kidd, *Dental Caries The disease and its clinical management*, "Caries removal and the pulpo-dential complex", Blackwell Munksgaard, Chapter 17, Quintessence Books (2003), 10 pgs.

Kneist and Heinrich-Weltzien, (2001), Tissue Preservation in Caries Treatment, Chap. 17; 205-219.

Paddick et al., (2005), *Appl. Environ Microbiol.*, 71:2467-2472.

Römpp Chemie Lexikon; 9th edition; (1995) pp. 3677-3678.

Sevcigan et al., IADR (2005), poster #2982; 1 page.

URL<http://en.wikipedia.org/wiki/Dental_caries>, 12 pages [Jan. 14, 2010].

URL<http://en.widipedia.org/wiki/Dental_plaque>, 2 pages [Jan. 14, 2010].

Eisenberg et al., "Associations of microbilolgical factors and plaque index with caries prevalence and water fluoridation status," Oral Microbiol. Immunol., 1991; 6:139-145.

Margolis et al., "Composition of Pooled Plaque Fluid from Caries-free and Caries-positive Individuals Following Sucrose Exposure," Journal of Dental Research, 1992; 71:1776-1784.

FDA, Select Committee on GRAS Substances (SCOGS) Opinion: Benzoic Acid. Last Updated Aug. 10, 2011, URL<http://www.fda.gov/Food/FoodingredientsPackaging/GenerallyRecognizedas-SafeGRAS/GRASSubstancesSCOGSDatabase/ucm260036.htm>.

Goshorn, R.H. et al., "Antiseptic and Bartericidal Action of Benzoic Acid and Inorganic Salts, Effect of pH" Industrial and Engineering Chemistry. Jun. 1938, vol. 30, No. 6, 646-648.

Gray et al., Kinetic Assay of Human Pepsin with Albumin-Bromphenol Blue as Substrate, Clinical Chemistry, vol. 29, No. 3, 1983, pp. 447-451.

\* cited by examiner

COLLAGENOLYTIC ACTIVE ENZYME CONTAINING COMPOSITIONS, AND THEIR USE IN THE DENTAL FIELD

This application is a divisional of U.S. application Ser. No. 11/128,553, filed May 13, 2005 now abandoned which claims priority to EP Application No. 04012256.6, filed May 24, 2004.

FIELD OF THE INVENTION

The invention relates to a composition comprising at least one collagenolytic active enzyme with enzymatic activity at acidic pH for drilless enzymatic caries removal. Furthermore, the present invention relates to a process of producing such collagenolytic active enzyme comprising compositions and to processes of removing caries.

The invention also relates to the use of collagenolytic active enzymes in dental applications.

BACKGROUND

Caries, which is also called tooth decay, is one of the most frequently occurring human diseases. Caries is a bacterial damage of the tooth which may even cause teeth to fall out. From the outside, teeth are protected by a cover of hard enamel enclosing the softer dentin which, in turn, encloses the so-called pulp. The enamel itself consists of about 95% inorganic compounds, especially hydroxylapatite, and about 5% organic compounds and water. Dentin is softer than enamel and consists of about 65% inorganic compounds (mainly hydroxylapatite), about 20% organic compounds (mainly collagen and polysaccharides) and about 15% water.

A caries disease often starts with the formation of plaque and tartar which develops from plaque. Plaque is a whiteish film on the tooth which mainly consists of a bacteria, proteins, and polysaccharides containing mass which is difficult to wipe off. The term "plaque" describes all microorganisms present on the surface of the tooth and their organic matrix. From plaque, caries and tartar can develop, the latter of which is so damaging to the gums and consists of calcified plaque. Even with careful brushing, tartar cannot be removed from the surface of the tooth.

Caries develops in several steps by bacterial fermentation of carbohydrates, in particular by bacterial fermentation of sugar to acids. The acids resulting from said bacterial fermentation firstly dissolve the hard enamel, whereas bacteria attack mainly the organic components such as food particles having remained on the teeth.

If the enamel becomes porous and soft by the bacteria induced influence of acids, bacteria may reach the dentin layer below the tartar and infect it with caries. A caries disease often results in an inflammation of the pulp under the dentin. An inflammation of the pulp is extremely painful and may cause a serious risk to the health of the patient if it is not treated quickly.

The region, where the enamel or enamel and dentin are dissolved the most, is called the caries lesion. A caries lesion normally consists of a multitude of distinct compounds, partly of bacterial origin, partly of tooth debris, and partly coming from saliva as well as from food particles.

Unlike other living body tissue, there is no endogenous way of repairing tooth damage caused by caries. Only in the early phase of caries healing by means of re-mineralisation of the hard substance of the tooth is possible. At a later stage of caries, there is a need for a treatment, wherein a region of the tooth damaged by caries is removed. The empty space resulting from removing the caries affected tooth tissue is called cavity. Upwards from a certain size of a cavity and after the caries affected tooth tissue has been removed the cavity is normally filled with an artificial filling.

The damage of the tooth caused by caries are normally removed by drilling out the carious tooth tissue with a dental drill. Depending on indication and technique, drill velocities of up to 400,000 rpm are obtained. The drills used are hard metal or diamond instruments. Since drilling causes an enormous release of heat and the removed tooth substances contaminate the site of the treatment, a mixture of water and air is usually required to cool and clean the cavity.

However, this method of treatment for removing caries using a dental drill has several disadvantages.

A serious disadvantage, for example, is that this method of treatment is generally associated with considerable pain for the patient. As pain caused by drilling, the patient feels especially the fine vibrations of the rotating drill instruments at the regions of the tooth which are often inflamed. Additionally, there is a whistling drill sound which is perceived as being very unpleasant. Therefore, many patients often wait too long before they have a tooth treated which is affected and damaged by caries.

A further disadvantage regarding this method of treatment is that drilling damages and removes healthy tooth substance. Such a removal of the healthy tooth material, however, is generally undesirable. Moreover, a mechanical treatment of caries with a drill can seriously damage the tooth. Often, the carious tissue in a caries lesion has damaged the healthy tooth to an extent, where only a small amount of healthy dentin separates the caries lesion from the pulp. In such cases, the dentist is faced with the very difficult task of completely removing carious regions without damaging the fragile dentin wall covering the pulp. Often, damaging opening the pulp cannot be avoided since the mechanical resistance of the remaining dentin layer covering the pulp is not strong enough to resist even low mechanical stress.

In addition to the classical drilling therapy described above, an increasing number of methods for the gentle treatment of the hard substance of the tooth have been described in the last few years.

WO 98/20838, for example, describes a chemo-mechanical method for removing caries essentially pain-free and without a drill. In order to dissolve caries, the aggressive oxidizing agent sodium hypochlorite is used in combination with amino acids. A disadvantage of this method is that sodium hypochlorite, as a strong oxidizing agent, reacts unspecifically with constituents of infected carious tooth tissue and non-infected healthy tooth tissue.

Furthermore, this method allows only softening of the carious regions at the surface. As soon as the oxidizing effect decreases, the sodium hypochlorite solution must be applied again. Therefore frequent application of the solution is necessary.

Clinical experience demonstrates that the described chemo-mechanical method is very time-consuming and not always successful so that in the end, one nevertheless has to go back to a dental drill.

WO 96/07329 describes a method for treating and preventing caries and periodontal diseases. It suggests a particular way of fighting germs in the oral cavity with enzymes obtained through genetic engineering. Lysozyme and dextranase are mentioned as suitable enzymes. As a starting point for treating and preventing caries, plaque shall be removed with the enzymes. The treatment of caries as such is not mentioned in the document.

Often, enzyme containing treatment compositions can be useful which are adjusted to a pH value at which enamel and dentin are attacked and degraded. This, for example, can be the case if a caries lesion is located under a perforated but not completely destroyed enamel cover. In such cases, it may be desirable to be able to remove the enamel cover without a drill. This can be achieved by applying an acidically adjusted enzyme containing treatment composition wherein the acid attacks and removes the perforated, but not completely destroyed, enamel cover and the enzyme comprised in such a composition induces or carries out the degradation of the carious regions located under the enamel cover. Furthermore, due to the degrading effect of such an acidic composition on dentin and enamel a roughening of the insides of the cavity could be achieved thereby preparing and facilitating a subsequent filling therapy.

Generally, dentists can rely on various methods for the decision, whether a cavity is "clean", i.e., free of carious residues. Routinely, however, dentists rely on a distinct acoustic signal being generated by scratching the surface of a freshly prepared cavity with a dental probe. Caries free dentin emits a crisp, clear sound when being scratched with such a dental probe, resulting from a high fraction of mineral material in the cavity walls. While this test is often applied as the most easy way of determining whether a cavity is free of carious material and the reliability of this test is high, it does not necessarily determine exactly the point of removal of tooth material at which the cavity can be defined as being free of caries. Usually, for applying the dental probe method with the desired result, the amount of material to be removed from the tooth is higher than necessary. This can be explained by the fact that slightly demineralized tooth material, which is free of caries bacteria but already partially demineralized, can be treated like healthy tooth material but does not give the typical scratching sound when scratched with a dental probe.

It has thus been a long felt need, to have a choice of materials for the removal of caries from a cavity without using a dental drill, which either remove the caries and leave softer, but healthy tooth material basically untouched or remove caries and softened, partly demineralized dental material in order to be able to rely on the dental probe scratch test.

DE 102 37 317 A1 describes a solution based on pepsin for the treatment of caries. A drawback of pepsin can sometimes be found in its unspecific enzymatic activity, occasionally resulting in the necessity of providing high amounts of pepsin in formulations of solutions for the treatment of caries. Furthermore, because of its animal origin, pepsin can show an inherent instability at elevated temperatures which may compromise thermal stability of chemical formulations with pepsin. Additionally, due to its animal origin, pepsin in medical applications necessitates a complex and therefore expensive regulatory process.

H. Oyama et al. describe in *J. Biochem.* 131, 757-765 (2002) a CLN2-related and thermostable serine-carboxylproteinase, its cloning, expression and identification of catalytic serine residue.

The crystal structure of kumamolysin is described in Structure, Vol. 10, 865-876, June, 2002.

A collagenolytic serine-carboxylproteinase from *Alicyclobacillus sendaiensis* strain NTAP-1, its purification, characterization, gene cloning, and heterologous expression is described in *Applied and Environmental Microbiology*, January 2003, p. 162 to 169.

JP 2002078489A relates to novel acid protease where serine residue participates in activity expression.

U.S. Pat. No. 6,465,236 B1 describes a thermostable collagen-digesting enzyme, a novel microorganism producing the enzyme and a process for producing the enzyme.

None of the latter documents describes a composition which would be fit to be used in dental applications.

Enzyme containing solutions also often have the major drawback of lack of thermostability. Since enzymes are very sensitive to temperatures above their denaturation temperature, many compositions containing enzymes must be stored and transported in a temperature conditioned environment. This is especially disadvantageous when such enzyme containing compositions are designed to be used also in areas where there may be a lack in energy infrastructure and maintaining an intact cooling chain during transport or storage is impossible. Furthermore, also in countries where there is only a minimal risk of a broken cooling chain it is desirable to be able to store enzyme containing compositions under ambient conditions without risking damage to the composition.

Therefore there is a need for a composition with which caries infected tooth tissue can be removed in daily practice in a simple, pain-free, effective and inexpensive manner. Furthermore, there is a need for a composition for removing caries with which the healthy tooth material worthy to be preserved is not (or not more than avoidable) attacked and damaged. Moreover, there is a need for a composition for removing caries which ensures that after the treatment of caries essentially no live bacteria remain. Moreover, there is a need for a composition for the drilless removal of caries which reduces the required amount of enzymes. Additionally, there is a need for a composition for the drilless removal of caries which can be transported and stored an ambient conditions or even at elevated temperatures without showing a significant decrease in activity.

In one aspect, the present invention relates to a composition comprising at least one collagenolytic active enzyme, at least one solvent and at least one acid, wherein said composition has a collagenolytic activity of more than about 5 U/ml.

A composition according to the invention contains at least one enzyme belonging to the group of collagenolytic active enzymes. Such collagenolytic active enzymes are also often described as collagenases. In the context of the invention, a collagenolytic active enzyme is an enzyme which will digest the triple-helical native collagen fibers.

Generally, all types of collagenolytic active enzymes can be employed according to the present invention. It has, however, in some cases been found to be advantageous if at least one collagenolytic active enzyme is employed which is thermally stable. The term "thermally stable" in the context of the invention refers to enzymes, which show collagenolytic activity after storage at a temperature of at least 40° C., or at least 50° C. or at least 55° C. or at least 60° C. or at least 65° C. or at least 70° C. or at least 75° C. or at least 80° C. for 1 hour.

In another aspect of the present invention, at least one enzyme can be employed, which is activated by Ca-ions. It has been found to be advantageous, if a composition according to the present invention contains at least one collagenolytic active enzyme, which can be activated by Ca-ions. The presence of such an enzyme in a composition can have a positive effect on the efficiency of caries removal in a caries lesion. While the acid present in the composition dissolves mineral structures in the caries lesion, Ca-ions can be generated and access for the collagenolytic enzymes to collagen structures may be provided. Due to the activation of the collagenolytic enzymes by the Ca-ions, the digestion of collagen in the lesion can be improved and the process of caries removal can be substantially accelerated.

Generally, all collagenolytic active enzymes which are active in the acidic pH region can be used as constituents of the compositions according to the invention. In one embodiment of the invention, however, a serine-carboxyl proteinase is used as a collagenolytic active enzyme.

Serine-carboxyl proteinases are a subclass of carboxyl proteinases. Serine-carboxyl proteinases which can be used according to the invention are characterized by a high specificity for collagen and are showing their maximum proteolytic activity in the acidic pH regime. A class of serine-carboxyl proteinases which is useful in the context of the invention is the class of sedolisines. Sedolisines are described in detail by Alexander Wlodawer et al. in Acta Biochimica Polonica Vol. 50, No. 1/2003, pp. 81-102, which is incorporated herein by reference and is expressly mentioned as a source for disclosure on the above mentioned sedolisines. The disclosure of the latter document with regard to sedolisines is regarded as being part of the disclosure of the present text.

The collagenolytic active enzymes used in the invention generally may be isolated from plants, animals or fungi as well as from bacteria, archaea or yeasts. They may also be produced via genetic engineering. In another embodiment of the invention a composition for the drilless caries removal comprises at least one collagenolytic active enzyme which is of non-animal origin.

Generally, all types of collagenolytic active enzymes, especially of serine-carboxyl proteinases, can be used in a composition according to the invention. Preferably at least one collagenolytic active enzyme is present in the composition which is able to assist in the drilless removal of caries from a tooth. Among the number of collagenolytic active enzymes which are able to fulfil this task, especially useful according to the invention are the serine-carboxyl proteinases like sedolisin, kumamolisin As, sedolisin-B, kumamolysin, kumamolysin-B, sedolisin-xApB, physarolisin, physarolisin-B, human tripeptidyl-peptidase and ScP-A or other pepstatin-insensitive proteinases like Wai21a. Therefore, according to another embodiment of the invention a composition comprises at least one serine-carboxyl proteinase selected from the group consisting of sedolisin, sedolisin-B, kumamolysin, kumamolysin-B, sedolisin-xApB, physarolisin, physarolisin-B, human tripeptidyl-peptidase and ScP-A.

Kumamolysin and ScP-A are most preferably obtained from thermophile bacteria *Bacillus novosp.* MN-32 and/or *Alicyclobacillus sendaiensis* strain NTAP-1. Therefore, according to a further preferred embodiment of the invention at least one collagenolytic active enzyme present in a composition is obtainable from *Bacillus novosp.* MN-32 or *Alicyclobacillus sendaiensis* strain NTAP-1.

A detailed description of processes for the production of serine-carboxyl proteinases and such serine carboxyl proteinases can be taken from H. Oyama et al. in *J. Biochem.* 131, 757-765 (2002), Structure, Vol. 10, 865-876, June, 2002, *Applied and Environmental Microbiology*, January 2003, p. 162 to 169, JP 2002078489A and U.S. Pat. No. 6,465,236 B1. All cited documents are expressly mentioned and their disclosure with regard to serine-carboxyl proteinases, their production and their characteristics are regarded as being part of the disclosure of the present text.

A composition according to the invention can comprise one collagenolytic active enzyme, e.g., one serine-carboxyl proteinase or another pepstatin-insensitive proteinase, or two or more collagenolytic active enzymes, e.g., two or more serine-carboxyl proteinases, e.g., 3, 4, 5, 6 or 7 collagenolytic active enzymes, e.g., serine-carboxyl proteinases. It is, however, preferred, if the number of collagenolytic active enzymes is 1, 2, 3 or 4, especially 1, 2 or 3.

A composition according to the invention comprises at least one solvent. Generally, each solvent in which enzymes can be dispersed or dissolved without being denaturalized can be a component comprised in the composition according to the invention. All aqueous and organic solvents can be used which do not impair the activity of the enzymes to an extent that their use according to the invention is made impossible.

Suitable solvents are, for example, water, linear, branched or cyclic, saturated or unsaturated alcohols with 2 to about 10 C atoms, ketones, esters, carboxylic acids and mixtures of two or more of said types of solvents.

According to the invention, for example dialkyl ketones or alcohols or polymerizable substances of low viscosity such as polyethylene glycol (PEG), hydroxyethyl methacrylate or (2,3-epoxypropyl) methacrylate and mixtures thereof can be used as solvents. Especially preferred alcoholic solvents are methanol, ethanol, isopropanol, and propanol. Other suitable organic solvents are glycerin, dimethyl sulfoxide, tetrahydrofurane, acetone, methyethyl ketone, cyclohexanol, toluene, methylen chloride, chloroform, alkanes and acetic acid alkyl esters, in particular acetic acid ethyl ester.

Generally, it is possible to use the above-mentioned solvents alone or as a mixture of two or more of any of these solvents if the solvent mixtures do not impair the enzyme activity to such an extent that the desired result cannot be obtained. Preferred solvent mixtures according to the invention are comprising water as a component, in particular preferred are aqueous-alcoholic solvent mixtures.

Generally it is possible to use the above-mentioned solvents alone or as mixture of two or more of any of these solvents if the solvent mixtures do not impair the enzyme activity to such an extent that the desired result cannot be obtained. According to a preferred embodiment of the invention, however, solvent mixtures are used comprising water as a component, in particular aqueous-alcoholic solvent mixtures.

The viscosity of the compositions according to the invention can be essentially within any ranges, from highly fluid to pasty, in case the compositions contain solvent. Often times it has turn out to be useful if the compositions have a sufficiently low viscosity on order to flow even into not easily accessible regions within a caries lesion to be treated. However, it can be also advantageous, for example in case when the caries lesion is located at a region at the side of the tooth, if the solvent containing composition according to the invention has a higher viscosity, i.e. if the composition is gel-like, so that the composition does not flow away too quickly.

A composition according to the invention comprises at least one acid. Generally, a composition as described above can contain any type of acid, organic or inorganic, or mixtures of both types of acids, in order to provide the desired pH value. It has been found to be possible to use organic acids like diethylbarbituric acid, tris(hydroxymethyl) amino methane (TRIS), glycine, glycylglycine, N-(2-acetamido)-2-aminoethane sulfonic acid (ACES), N-(2-acetamido)-imino diacetate (ADA), N,N-bis(2-hydroxyethyl)-2-aminoethane sulfonic acid (BES), N,N-bis(2-hydroxyethyl) glycine (BICINE), 2,2-bis(hydroxyethyl)-imino tris(hydroxymethyl) methane (BIS-TRIS), 2-(cyclohexyl amino)ethane sulfonic acid (CHES), 2-[4-(2-hydroxyethyl-1-piperazine)]ethane sulfonic acid (HEPES), 3-[4-(2-hydroxyethyl-1-piperazinyl)]propane sulfonic acid (HEPPS), 2-morpholinoethane sulfonic acid (MES), 3-morpholinopropane sulfonic acid (MOPS), piperazine-1,4-bis(2-ethane sulfonic acid) (PIPES), N-[tris(hydroxymethyl)-methyl]-2-aminoethane sulfonic acid (TES), N-[tris(hydroxymethyl)-methyl]-glycine (TRICINE) to shift the pH value of a composition according to the present invention into the desired pH range. It has to be noted, however, that some or all of the above-mentioned acids can, besides lowering the pH value, have other effects on the composition, especially acceleratory or inhibitory effects. It is also within the context of the invention that combinations of the above-mentioned acids are used, wherein one or more acids are added for the purpose of reaching or adjusting a desired pH value and one or more acids are added for other purposes, irrespective of their influence on the pH value.

It has, however, been discovered that inorganic acids such as sulfuric acid, sulfonic acid, phosphoric acid, polyphosphonic acids, hydrochloric acid, formic acid, acetic acid, propionic acid, citric acid, lactic acid, oxalic acid or nitric acid and the like are advantageous in providing the desired pH value and improving the denaturalizing and mineral dissolving properties of the composition according to the invention. It has to be noted that in the context of the invention acids like formic acid and acetic acid are treated as being part of the group of inorganic acids.

It is possible to use combinations of the above-mentioned organic acids with inorganic acids for the purpose of lowering the pH value. It has, however, been found sufficient or even advantageous, if the desired pH value is adjusted by using inorganic acids, especially phosphoric acid.

Moreover, an inventive composition can comprise at least one buffer or a first compound which when combined with a second compound acts as a buffer. The buffer comprised in an inventive composition serves to adjust the pH value in an inventive solution comprising an inventive enzyme mixture to a value desired for the respective embodiment of the invention and for preventing a change of the pH value during a defined period of time and for stabilizing the respective solution, respectively.

In the context of the invention, all customary buffer are suitable, such as phosphate buffer, carbonate buffer, acetate buffer, citrate buffer, tris buffer, glycylglycine buffer or glycine buffer. Sodium phosphate buffer, sodium hydrogen phosphate buffer, sodium dihydrogen phosphate buffer, potassium phosphate buffer, potassium hydrogen phosphate buffer, potassium dihydrogen phosphate buffer or pyrophosphate buffer are preferred. Suitable are also sodium carbonate buffer, potassium carbonate buffer, sodium hydrogen carbonate buffer or potassium hydrogen carbonate buffer. Especially preferably the inventive compositions comprise phosphate buffer and their components, respectively. An especially preferred phosphate buffer is a sodium dihydrogen phosphate buffer.

The buffer concentration of a solvent containing inventive solution can be in the range of up to about 100 mol per liter. The concentration mol per liter relates to the acidic fraction in the solution. A range of from about 0.001 to about 10 mol per liter is preferred. According to another embodiment of the invention an enzyme containing solution comprises a buffer in the range of about 0.001 mol per liter to about 5 mol per liter. The range of from about 0.01 to about 3 mol per liter is preferred, while the range of from about 0.02 to about 1.0 mol per liter is more preferred. According to another embodiment of the invention an enzyme containing solution comprises a buffer in the range of from about 0.03 to about 10 mol per liter, more preferred in a range of from about 0.05 to about 5 mol per liter and even more preferred of from about 0.02 to about 1.0 mol per liter.

A solution comprising an inventive enzyme mixture generally can have a pH range of from about 1 to about 5.

According to another embodiment of the invention the pH value of an enzyme containing solution according to the present invention can be in the range of from about pH 1.5 to about pH 4.9, in particular of from about pH 2 to about pH 4.5, in particular of from about pH 2.5 to about pH 4.0.

The enzymatic activity of enzymes is usually characterized using so called enzyme units [U]. An enzyme unit is the respective amount of an enzyme or a mixture of two or more enzymes which is necessary to convert one $\mu$mol of a corresponding enzyme substrate per minute at standard conditions. A collagenolytic active enzyme comprising composition according to the invention generally contains the collagenolytic active enzyme or a mixture of two or more of those collagenolytic active enzymes in an amount of more than about 5 U/ml of composition, with regard to the collagenolytic activity of the enzyme or the enzyme mixture. It is, however, preferred if the activity of the collagenolytic active enzyme or the activity of a mixture of two or more of those collagenolytic active enzymes is adjusted to more than about 100 or more than about 150 or more than about 200 or more than about 255 U/ml of composition.

The enzyme solutions according to the invention can have, for example, total enzyme activities of from about 5 U to about 1,000,000 U per ml solution. The lower limit is, for example, about 5, 7, or 10 U/ml wherein the inventive effect is normally considerably improved at a lower limit of the total enzyme activity of about 20 or about 25 or about 30 or about 40 or about 45 or about 50 U/ml solution.

Preferably the inventive enzyme solutions comprise about 60 U to about 600,000 U/ml solvent, for example about 100 U to about 400,000 U/ml solvent or about 300 to about 300,000 U/ml solvent or about 500 U to about 200,000 U/ml solvent or about 700 to about 150,000 U/ml solvent or about 1,000 to about 100,000 U/ml solvent or about 5,000 to about 50,000 U/ml solvent. Moreover, in the context of the present description, the described lower limits of the respective ranges can be combined with each of the above-mentioned range limits if the advantageous effect of an inventive enzyme solution occurs especially distinctly within such a range.

The enzymatic activities given here always relate to the respective standard conditions for the respective enzyme. In this context, the following standard conditions are valid:

| | |
|---|---|
| Kumamolysin: | The activity was determined according to the method described by N. Tsuruoka et al. in Applied and Environmental Microbiology, January 2003, p. 163, left col., under "Enzyme assay (i) Method I and (ii) Method II. |
| ScP-A: | The activity was determined according to the method described by N. Tsuruoka et al. in Applied and Environmental Microbiology, January 2003, p. 163, left col., under "Enzyme assay (i) Method I and (ii) Method II. |
| Pepsin: | 1 unit corresponds to a $\Delta E$ of 0.01 at A280 nm at 37° C. of converted hemoglobin with TCA. |

The high specificity of Kumamolysin and ScP-A for collagen can reduce the amount of enzymes needed to obtain comparable results when using less specific enzymes. Nevertheless it may be advantageous to combine the enzymes with a high specificity for collagen like Kumamolysin and/or ScP-A with enzymes with a lower specificity for collagen, e.g., any other proteinase which is at least to a certain extent able to digest collagen. Generally, all proteinases can be applied which do not impair the overall enzymatic activity of the composition according to the invention to such an extent that the desired result cannot be obtained. Therefore, according to a further embodiment of the invention a composition can contain at least one further proteinase.

This further protease is preferably active at a pH below pH7. Upon treatment of carious dentin, the acid, the collagenase active at acidic pH and the further protease active at acidic pH act synergistically. The acid dissolves remnant hydroxyapatite present in the carious tissue making the collagen accessible to the enzymes. The collagenase splits the triple helical and denatured collagen and makes it thus more easily digestable for the further more unspecific protease which acts most efficiently on non-triple helical collagen. Furthermore the Ca made available by dissolution of hydroxyapatite in the lesion might act as an enhancer, stimulating the action of enzymes such as serine-carboxyl proteinases.

Since the composition according to the invention has an acidic pH it is preferred that at least one of said further proteinases has a catalytic activity also in the acidic pH region, i.e. is an acidic proteinase. Among those acidic proteinases, pepsin is the preferred enzyme. Pepsin can, e.g., be obtained from pig stomach. Therefore, according to a further embodiment of the invention a composition can contain at least one further proteinase or a mixture of two or more further proteinases, wherein at least one of said further proteinases is pepsin.

Generally, it will be desirable to optimize the overall performance of a composition according to the invention. For that purpose a composition according to the invention may contain additives. Therefore, in a further embodiment of the invention a composition can contain at least one additive.

Generally, all additives can be employed which do not or not more than avoidable impair the effect of a composition according to the invention. Appropriate additives can, e.g., be selected from the group consisting of thickening agents, rheological additives, polyhydric alcohols, inhibitors and buffers.

The viscosity of the compositions according to the invention can be essentially within any ranges, from highly fluid to pasty, in case the compositions contain solvent. Often times it has turn out to be useful if the compositions have a sufficiently low viscosity on order to flow even into not easily accessible regions within a caries lesion to be treated. However, it can be also advantageous, for example in case when the caries lesion is located at a region at the side of the tooth, if the solvent containing composition according to the invention has a higher viscosity, i.e. if the composition is gel-like, so that the composition does not flow away too quickly.

The viscosity ranges of the solution according to the invention are, for example, in a range of from about 0.5 mPa*s to about 100 Pa*s at +25° C. or, for example, in a range of from about 5 mPa*s to about 50 Pa*s at +25° C.

A collagenolytic active enzymes containing composition according to the invention can contain at least one rheological additive.

Generally it can be desirable to adjust the rheological properties of compositions according to the invention in order to facilitate their use under a multiplicity of circumstances. Thus, often rheological additives are added to a composition according to the invention in order to improve their viscosity or their flow behavior. It has furthermore been found that some dissolved acidic proteinases can undergo structural changes on passing through a pH value around their respective isoelectric points due to configurational and interaction effects. Due to those structural and interactional changes some acidic proteinases may tend to precipitate from a composition on approaching the isoelectric point. This, however, can result in a gradual decrease in activity of the respective acidic proteinases at pH values near or above the respective isoelectric points. This behavior, in turn, may be counterproductive to one of the objects of the invention, namely the removal of collagenous residues in the cavity of a tooth while leaving the mineral components of the cavity walls basically untouched. It can thus be desirable to keep up the activity of acidic proteinases as long as possible and to avoid precipitation of acidic proteinase molecules on approaching the isoelectric point. Also when a combination of two or more proteinases is employed in the present case it can be possible that one of the proteinases in the mixture shows the behavior described above while another proteinase does not show this behavior. This might be the case when a composition contains a collagenolytic active enzyme together with pepsin.

It has been found in some cases that the addition of theological additives might inhibit such an early precipitation and facilitate prolonged action of the acidic proteinases even at higher pH values.

As theological additives, organic thickening agents are successfully used. Suitable theological additives are polysaccharides. It is thus preferred, when a collagenolytic active enzymes containing composition according to the invention contains a polysaccharide as a theological additive. Suitable polysaccharides are, for example, starch, mannan, xanthan, alginate, carragen, pectin, polyvinyl pyrrolidone, hydroxyethyl propylcellulose, hydroxybutyl methylcellulose, hydroxypropyl methycellulose, hydroxyethylcellulose or sodium carboxymethylcellulose and mixtures of two or more thereof. It has to be noted, that the term "theological additive" and the term "thickening agent" can be used interchangeably in the context of the present text, unless explicitly stated otherwise.

Generally, all thickening agents known by the person skilled in the art are suitable to adjust the desired viscosity of a composition according to the invention, if said thickening agents do not or at least not essentially impair the desired purpose of use. Further suitable thickening agents are, for example, polyethylene glycol, and inorganic thickening agents such as silica gels or phyllosilicates and mixtures of two or more of the mentioned thickening agents.

The viscosity of the compositions according to the invention can be essentially within any ranges, from highly fluid to pasty. Often it has turned out to be useful if the compositions have a sufficiently low viscosity in order to flow into regions not easily accessible within a caries lesion to be treated. However, it can also be advantageous if the composition according to the invention has a higher viscosity, i.e. if the composition is gel-like so that it does not flow away too quickly when the caries lesion is located at a region at the side of the tooth.

A composition according to the invention may contain a theological additive in an amount of about 0.1 to about 2 wt.-%, based on the weight of the composition. It is preferred, when the amount of theological additive is in a range of about 0.2 to about 1 wt.-%.

The rheological additives may serve to provide a composition whose viscosity is in the range of about 1 to about 1000 mPas at 25° C. It is preferred that a composition according to the invention has a viscosity of about 5 to about 500 mPas or about 10 to about 100 mPas at 25° C.

The viscosity is measured according to standard procedures with a Haake rheometer (RotorVisco (RV1); sensor (60/1°Ti) at 25° C.

Additionally to the above-mentioned rheological additives a composition according to the invention may contain a polyether or a zwitterionic tenside, or a mixture of two or more polyethers and zwitterionic tensides.

The addition of both types of components, or a mixture of them, has shown to improve the inhibition of precipitation even further.

Generally all types of polyethers are suitable for the purpose of inhibiting the precipitation of acidic proteinases. It is a prerequisite, however, that the polyethers used are, at least to a certain extent, water-soluble.

Generally, suitable polyethers should have a solubility in water at a temperature of 20° C. of at least about 1 g/l, preferably more, for example, at least about 5 or at least about 200 g/l. It is preferred, if polyethers used as a constituent of the compositions according to the invention exhibit a solubility in water of at least about 0.1 wt.-%, preferably at least about 1 wt.-% or at least about 2 wt.-% at 20° C.

Suitable polyethers are generally made by reacting a starting material, usually water, alcohol or amine, with one or more epoxides in a base catalyzed, ring opening reaction. It is also possible to obtain suitable polyethers by ring opening polymerization of cyclic ethers like tetrahydrofuran (THF). Preferred starting materials are water or mono- or polyfunctional alcohols. Suitable monofunctional alcohols are linear or branched, saturated or unsaturated aliphatic, cycloaliphatic or aromatic alcohols with 1 to about 22 carbon atoms, e.g., methanol, ethanol, n-propanol, isopropanol, n-butanol, isobutanol, tert.-butanol, the isomeric pentanols, the isomeric hexanols, the isomeric heptanols and their higher homologues, cyclohexanol, phenol, naphthol and the like. Among the preferred polyfunctional alcohols are alcohols with 2, 3 or 4 hydroxyl groups, e.g., ethylene glycol, propylene glycol, butylene glycol, trimethylolpropane, triethylolpropane, pentaerythritol, sorbitol, xylitol and the like.

Suitable epoxides or cyclic ethers in general are oxirane (ethylene oxide), propylene oxide, butylene oxide or THF.

Polyethers, which exhibit an inhibitory effect on the precipitation of acidic proteinases according to the invention can comprise only one type of monomers. It is, however, also within the scope of the invention to employ polyethers which are comprised of more than one type of monomer. Such copolymers can be organized randomly or in blocks.

It is preferred within the invention to employ a polyether which is mainly or completely comprised of ethylene oxide repeating units ($-CH_2-CH_2-O$) and has two or three hydroxyl groups.

The average molecular weight (Mw) of such polyethers, as measured by conventional methods like GPC, should not exceed about 10,000 atomic units, preferably it should be less than about 1,000 atomic units. The minimum average molecular weight (Mw) of such polyethers should be about 100 atomic units, preferably 150 atomic units or more, e.g. about 200 atomic units.

According to a preferred embodiment of the invention, a collagenolytic active enzymes composition can contain polyethylene glycol with a molecular weight of about 100 to about 500 atomic units, preferably about 200 atomic units.

Instead of or additionally containing one or more of the above-mentioned polyethers, a collagenolytic active enzymes containing composition according to the invention can contain one or more zwitterionic compounds. Generally, all types of low molecular components bearing at least one positively charged ion and one negatively charged ion are suitable in the present context. The term "low molecular" relates to zwitterionic components with a molecular weight of less than about 1000, preferably less than about 500. In a preferred embodiment of the invention, a collagenolytic active enzymes containing composition according to the invention contains one or more of the components glycine betaine, betaine, taurine, ectoines or dimethylsulfonium propionate as a zwitterionic compound.

Furthermore, a collagenolytic active enzymes containing composition according to the invention can contain one or more polyhydric alcohols with four or more hydroxyl groups which are not polyethers. Suitable polyhydric alcohols or sugar alcohols like are pentaerythritol, xylite, sorbitole, glucose, sucrose, fructose, mannitol or glycerol.

The collagenolytic active enzymes containing composition according to the invention can contain a polyether or a mixture of two or more polyethers in an amount of about 0.1 to about 20 wt.-%, based on the weight of the composition. It has, however, been found to be advantageous if the polyether is present in an amount of about 0.5 to about 8 wt.-%, especially in an amount of about 0.8 to about 5 wt.-%.

If the collagenolytic active enzymes containing composition according to the invention contains a zwitterionic compound or a mixture of two or more zwitterionic compounds, such components are present in an amount of about 0.1 to about 20 wt.-% based on the weight of the composition.

Generally, it has been found to be advantageous if zwitterionic components are present in an amount of about 1 to about 15 wt.-% or about 7 to about 12 wt.-%.

Since enzymes themselves are proteins, a proteinase containing composition is always in danger of losing its reactivity due to self digestion of the enzymes in the composition. The danger of self digestion can increase with decreasing specificity of the proteinase involved. While enzymes with a high specificity for a certain substrate protein usually can show only very slow self digestion or no self digestion at all, as long as the enzyme itself is not among the substrates, less specific proteinases can show an increased activity with regard to digestion of different types of enzymes in a composition. Especially pepsin containing compositions which are stored at pH values of less than 4 can undergo a rapid decrease in activity. In order to delay this decrease in activity, an inhibitor can be added to such a composition. An additional or alternative method to delay this decrease inactivity may be storage of the solution at a pH at which pepsin is most active but still stable and the collagenase is also stable. This may be a pH above about pH 2.

While the inhibitor delays the self digestion of acidic collagenase in the composition, it also slows down the reactivity towards proteins in a cavity. It may, however, be desirable to have a composition with improved storage stability for the sacrifice of reactivity towards caries.

An acidic collagenase containing composition according to the invention can thus furthermore contain an inhibitor.

Preferred inhibitors are belonging to the group of aldehyde-type inhibitors, e.g. Ac-Ile-Pro-Phe-CHO Ac-Ile-Pro-Phe-CHO, or can be chosen from pseudo-tyrostatin, tyrostatin, chymostatin, AcIPF, AcIAF and many other known inhibitors.

In order to stabilize the pH value of a collagenolytic active enzyme containing composition according to the invention, such a composition can include a buffer system. Generally, buffer systems are known to the skilled person and have to be chosen in relation to the desired pH region which has to be buffered. Suitable buffer systems are, e.g., $H_2PO_4/H_3PO_4$, formic acid/formiate, acetic acid/acetate, citric acid/Na-citrat, glycine/HCl.

The buffer concentration preferably lies in the range of about 0.01 to about 2.0 M.

Furthermore, in addition to the above mentioned additives a collagenolytic active enzyme containing composition according to the invention may contain at least one further additive.

A collagenolytic active enzymes containing composition according to the invention can additionally contain preservatives. Generally, all types of preservatives which inhibit the growth of microorganisms in a composition according to the present invention and which are tolerated by the human body can be used. It has, however, been found that conventional preservatives of the para hydroxy benzoic acid ester type are most preferred. Especially preferred are preservatives known under the names methyl para hydroxy benzoic acid ester (methylparabene) and propyl para hydroxy benzoic acid ester (propylparabene). Each of the cited preservatives can be used as the sole preservative in a composition according to the invention. It is, however, also possible to use combinations of such preservatives. The preservatives are generally used in an amount of about 0.001 to about 1 wt.-%, based on the weight of the composition. In a preferred embodiment of the present invention, preservatives are used in an amount of about 0.01 to about 0.25 wt.-%, based on the weight of the composition.

Furthermore, a collagenolytic active enzymes containing compositions according to the invention can contain other additives such as complexing agents, enzyme substrates or enzyme effectors.

In the context of the invention, complexing agents may serve to facilitate the access to the caries lesion by a supporting degradation of the hydroxyapatite. The complexing agents can also contribute to the cleavage of the cell-walls of the bacteria.

Preferred complexing agents of the present invention are those which form a stable complex with metal ions having a valence of 2. For example, EDTA (ethylen diamino tetraacetic acid), EGTA (ethylene glycol diamino ethyl tetraacetic acid), citric acid or salicylic acid or NTA (nitrilo triacetate) are suitable complexing agents. EDTA (ethylen diamino tetraacetic acid) is the most preferred complexing agent.

In the context of the invention, further compounds capable of optimizing the ability of the enzymes to function can be added to an inventive composition. Such enzyme activating or inhibiting compounds comprise diethylbarbituric acid, tris (hydroxymethyl) amino methane (TRIS), glycine, glycylglycine, N-(2-acetamido)-2-aminoethane sulfonic acid (ACES), N-(2-acetamido)-imino diacetate (ADA), N,N-bis(2-hydroxyethyl)-2-aminoethane sulfonic acid (BES), N,N-bis(2-hydroxyethyl) glycine (BICINE), 2,2-bis(hydroxyethyl)-imino tris(hydroxymethyl) methane (BIS-TRIS), 2-(cyclohexyl amino)ethane sulfonic acid (CHES), 2-[4-(2-hydroxyethyl-1-piperazine)]ethane sulfonic acid (HEPES), 3-[4-(2-hydroxyethyl-1-piperazinyl)]propane sulfonic acid (HEPPS), 2-morpholinoethane sulfonic acid (MES), 3-morpholinopropane sulfonic acid (MOPS), piperazine-1,4-bis(2-ethane sulfonic acid) (PIPES), N-[tris(hydroxymethyl)-methyl]-2-aminoethane sulfonic acid (TES), N-[tris (hydroxymethyl)-methyl]-glycine (TRICINE), acids such as sulfuric acid, sulfonic acid, phosphoric acid, hydrochloric acid, acetic acid, nitric acid, bases such as sodium hydroxide, potassium hydroxide, lithium hydroxide, ammonia, calcium hydroxide, magnesium oxide, salts such as magnesium chloride, magnesium sulfate, magnesium nitrate, calcium chloride, calcium sulfate, calcium nitrate, iron(III) chloride, iron (II) chloride, ammonium sulfate, sodium chloride, potassium chloride, sodium phosphates, potassium phosphates, co-enzymes, and vitamins.

The invention also relates to a process for the preparation of a composition according to the invention. Thus, the invention relates to a process of preparation a composition according to the invention, wherein at least one collagenolytic active enzyme, a solvent and an acid are mixed so that said composition has a collagenolytic activity of more than about 5 U/ml.

In a further embodiment, the invention relates to a process of preparation a composition according to the invention, wherein at least one collagenolytic active enzyme, an unspecific protease which is active at a pH of less than 7, e.g., pepsin, a solvent and an acid are mixed so that said composition has a collagenolytic activity of more than about 5 U/ml.

Regarding producing and storing in an inventive process the person skilled in the art generally can use all known techniques of how to treat enzymes. The composition according to the invention, for example, may be treated by means of chromatography techniques, freeze drying, spray drying, granulation, centrifugation, precipitation, crystallization or ultrafiltration or nanofiltration.

Moreover, all production adjuvants known by the person skilled in the art can be used to improve the storage stability.

The invention further relates to a process of removing caries wherein the enzyme containing composition as described in the context of the invention is applied to the region of a tooth affected by caries.

When selecting the suitable treatment solution, in particular the suitable enzymes in the solution, for the treatment of removing caries one has to consider, for example, which type of caries is present in the particular case.

Generally a difference is made between distinct types of caries. Therefore, for example, caries is classified as broken-down caries with unimpeded access to the dentin, caries lesions wherein carious dentin is still covered with enamel, enamel caries, caries of the neck of the tooth and caries of the root of the tooth.

If the spot affected by caries is enclosed with a thick layer of enamel or an old filling and thus is not accessible by the treatment solution, the enamel cover or the old filling may be removed with a fast rotating drill. If, however, the enamel cover is perforated, for example, by an advanced caries disease, it may by penetrated with a composition according to the invention combined with mechanical support without the use of a dental drill. Possible mechanical tools for supporting the penetration of perforated enamel covers comprise a micro-brush with a little brush made of plastics or metal, specimen with a metal tip, specimen with a spoon, specimen with a ball and other tolls generally available in a surgery of a dentist for dental use. These tools serve to spread the inventive solution over the site to be treated and to rub said solution in, to remove softened carious dentin and to tactilely make out hard surfaces of dentin and enamel by touch.

If access to the region of the tooth affected by caries is possible, the treatment can start with the identification of the carious regions of the tooth in the mouth of the patient. The identification can be carried out by methods known to the dentist, for example by inspection, probing, X-ray, but also by using diagnostic impression materials. The identified, caries infected regions of the tooth may be optionally roughly cleaned, for example with a probe or an excavator wherein also abrasion agents may be optionally added. Subsequently the region of the tooth to be treated can be rinsed and air-blown. These steps are purely optional and do not have to be part of a process for the treatment of caries according to the present invention.

The caries can be removed by applying the inventive enzyme containing composition onto the prepared region of the tooth.

The site to be treated as well as the optionally present cavity should be always covered and filled completely with the inventive solution, respectively. A suitable application volume for the treatment of a region of a tooth affected by caries can be, for example, about 100 µl. However, the suitable application volume should be adjusted to the particular case, i.e. the size of the cavity and the size of the region of the tooth affected by caries. Therefore, suitable application volumes may be in the range of from about 0.001 to about 0.5 ml, or in the range of from about 0.01 to about 0.3 ml or in the range of from about 0.02 to about 0.2 ml.

The preferred exposure time of the inventive enzyme containing composition can be in a range of from about 10 s to about 5 min wherein, depending on the size of the caries lesion, the exposure times can be reduced or enhanced. The exposure time can preferably be in the range of from about 15 s to about 3 min, for example in the range of from about 15 s to about 2 min or in the range of from about 20 s to about 1 min.

During the exposure time the carious parts of the caries lesion are degraded, and a larger cavity develops. Once the exposure time has ended, the treated region of the tooth may be rinsed and optionally air-blown.

The caries degrading treatment step is carried out, for example, according to the following scheme. A suitable application volume of the enzyme containing solution is applied onto the region of the tooth to be treated, the solution can be exposed for 5 s to about 5 min, and subsequently, the region of the tooth may be rinsed with water, for instance. In the following, such a treatment process is referred to as incubation step.

Generally the incubation step can be carried out as often as necessary so that no carious residues remain at the treated region of the tooth. The incubation step can be carried out once or more than once, for example twice or three times or even more often. In most cases, however, it will not be necessary to repeat the incubation step more than twice or three times.

In the context of the invention it turned out to be advantageous in some situations if the incubation step is carried out twice in succession. The duration of exposure of the inventive enzyme solution to the region of the tooth affected by caries should be about 20 to about 120 s, for example about 60 s.

Therefore, the invention also relates to a process of removing caries wherein an inventive composition, in particular an inventive composition comprising at least one solvent is applied to a carious region of a tooth.

Furthermore, the invention relates to a process of removing caries wherein said process is carried out in two or more incubation steps.

Moreover, the invention relates to a process of removing caries wherein in a first and in a further or several further steps an inventive composition is applied onto the caries region of a tooth.

In the context of the invention it turned out that in certain situations it might be advantageous to use an enzyme containing treatment solution which is adjusted to a pH value at which enamel and dentin are attacked and degraded. This, for example, can be the case if the caries lesion is located under a perforated but not completely destroyed enamel cover. In such cases it is possible to remove the enamel cover without a drill by means of an acidicly adjusted enzyme containing treatment solution wherein the enzyme comprised in such a solution induces or carries out the degradation of the carious regions located under the enamel cover.

In order to overcome the possible problems related to storage stability and loss of activity of collagenolytic active enzyme containing compositions according to the present invention it has been found that such collagenolytic active enzyme containing compositions can be advantageously provided in the form of a two component system.

The invention thus also relates to a composition comprising two components A and B, wherein component A comprises a collagenolytic active enzyme, e.g., a serine-carboxyl proteinase, preferably Kumamolysin or ScP-A, solvent and a buffer system and component B comprises a solvent, preferably water, a substance providing for a pH value of less than or equal to the pH value at which the collagenolytic active enzyme, e.g., the serine-carboxyl proteinase, preferably Kumamolysin or ScP-A, is most active after mixing A and B.

The collagenolytic active enzymes containing composition according to the invention can thus also consist of two components A and B. Component A comprises water and preferably a buffer system providing for a pH value above the pH value at which the acidic composition is most active. Generally, suitable buffer systems can provide for a pH value of about 3.5 or more, especially about 4 or more or about 4.5 or 5 or more. It has been found to be helpful, if component A has a pH value of more than about 5.2, especially more than about 5.3 or more than about 5.4. A pH value of about 5.5 has been found to give very good results.

The term "buffer system", as used in the present text, relates to a system being able to provide a buffering effect with regard to component A as well as a mixture of components A and B. It is thus not generally necessary, that component A contains a complete buffer system. It is sufficient, if a mixture of components A and B results in such a buffer system.

Generally, all types of buffer systems can be used, as described in the text above. In a preferred embodiment of the invention a phosphate buffer is used. Component A preferably contains a phosphate buffer at a pH value of about 4.5 to about 6. It has been found to give good results, if component A contains phosphate buffer in a concentration of about 10 to about 500 mmol/l, especially about 50 to about 150 mmol/l.

In a composition according to the present invention, component A preferably contains a collagenolytic active enzyme activity of less than about 60,000 U/ml, especially about 15 to about 50,000 or about 50 to about 45,000 U/ml composition. Generally, the remarks with regard to the collagenolytic active enzyme concentration and activity, e.g., the serine-carboxyl proteinase concentration and activity, as described in the above text are also valid for the presently described composition.

Component A generally can contain less than about 20 mg collagenolytic active enzymes, e.g., serine-carboxyl proteinase, preferably Kumamolysin or ScP-A, per milliliter of component A, preferably less than about 15 or less than about 10 mg/ml of component A.

Component A can further contain a rheological additive. Suitable are, for example, the theological additives as already described above. In a preferred embodiment of the present invention, component A contains a polysaccharide as a rheological additive, for example, hydroxyethylcellulose. Rheological additives can be present in component A in an amount of about 0.05 to about 1.5 wt.-%, preferably in an amount of about 0.1 to about 1 wt.-% or about 0.3 to about 0.7 wt.-%.

In another preferred embodiment according to the invention, component A can contain the following constituents in the following amounts:

| | |
|---|---|
| collagenolytic active enzyme: | about 0.1 to about 1.0 wt.-% |
| pepsin: | about 0.01 to about 1.0 wt.-% |
| sodium dihydrogenphosphate: | about 0.6 to about 2.4 wt.-% |
| sodium hydroxid: | about 0.001 to about 0.5 wt.-% |
| xanthan: | about 0.2 to about 1.0 wt.-% |
| methylparabene: | about 0.005 to about 0.05 wt.-% |
| propylparabene: | about 0.005 to about 1.0 wt.-% |
| water: | ad 100 wt.-% |

Component B according to the present invention comprises preferably water, an acid providing for a pH value of less than 4.0, a thickener and optionally a polyether or a zwitterionic tenside or a mixture of polyethers and zwitterionic tensides.

Generally, component B can contain all types of acids which have been mentioned above for reaching a desired pH value. Since components A and B can form a buffer system after mixing, it can be advantageous if at least one acid in component B matches a salt contained in component A. In a preferred embodiment of to the invention component B contains phosphoric acid. It has further been found to be advantageous, if component B contains the acid in such an amount that a pH value of about 2 to about 4.2, or about 2.5 to about 3.5 is reached after combining components A and B.

Component B can further contain a polyethyleneglycol or a zwitterionic compound or both. As polyethylene glycols, the above mentioned polyethylene glycols are suitable. It is preferred to use polyethylene glycol in the above specified range of molecular weights. If component B contains polyethylene glycol, the amount is within the range of about 0.1 to about 10.0 wt.-%, preferably about 0.5 to about 5.0 wt.-%, based on the weight of component B.

If component B contains the zwitterionic compound, the above-mentioned zwitterionic components are preferred. The amount of zwitterionic compounds in component B is in range of about 0.1 to about 20 wt.-%, especially about 1 to about 15 or about 7 to about 12 wt.-%.

In a preferred embodiment according to the invention, component B can contain the following constituents in the following amounts:

| | |
|---|---|
| sodium dihydrogenphosphate: | about 10 to about 20 wt.-% |
| phosphoric acid: | about 5 to about 10 wt.-% |
| polyethylene glycol: | about 2 to about 5 wt.-% |
| xanthan: | about 0.2 to about 1.0 wt.-% |
| water: | ad 100 wt.-% |

Component A and component B can contain one or more of the above-mentioned additives. Preferably one of components A or B contains at least one colorant in order to be to discriminate between the components and to be able to determine whether the components were thoroughly mixed before application.

The ratio in which components A and B are mixed, largely depends on the desired properties of the mixture. Generally, the components must be mixed in such a way that the pH value of the mixture is below the pH value of component A. Preferably, the ratio is chosen such that the properties of the mixture correspond to the properties described above for the collagenolytic active enzymes containing composition. It is thus possible, that components A and B are mixed in a ratio which leads to a mixture having a pH value of less than about 4, e.g., less than about 3.8 or less than about 3.5, or less than about 3.3 or less than about 3.2.

It is further preferred, when a mixture of components A and B has the following properties:

| | |
|---|---|
| pH value: | about 2.5 to about 3.5 |
| viscosity: | about 10 to about 50 mPas |
| serine-carboxyl proteinase activity: | about 1,000 to about 10,000 |
| buffer capacity: | about 0.5 to about 2.0 |

Components A and B are advantageously prepared such that in order to arrive at a mixture for application with the above-mentioned properties the ratio of components A and B is about 5:1 to about 1:5, especially about 2:1 to about 1:4 or about 1:1 to about 1:3.5, preferably about 1:2 to about 1:3.

A further embodiment of the invention relates to the method for the treatment of caries, wherein two components A and B as described above are mixed and a caries lesion is contacted with this mixture.

A further embodiment of the invention relates to the use of the mixture comprising components A and B, wherein component A comprises a collagenolytic active enzyme, e.g., a serine-carboxyl proteinase, preferably Kumamolysin or ScP-A, water, a buffer system providing for a pH value above the pH value at which the composition is most active and a theological additive and component B comprises water, an acid providing for a pH value of less than the pH value at which the collagenolytic active enzyme is most active, a thickener and optionally a polyether or a zwitterionic tenside or a mixture of polyethers and zwitterionic tensides, for the treatment of caries.

A further embodiment of the invention relates to the use of the composition comprising components A and B, wherein component A comprises a collagenolytic active enzyme, e.g., a serine-carboxyl proteinase, preferably Kumamolysin or ScP-A, water, a buffer system providing for a pH value above the pH value at which the composition is most active and a theological additive and component B comprises water, an acid providing for a pH value of less than the pH value at which the collagenolytic active enzyme is most active, a thickener and optionally a polyether or a zwitterionic tenside or a mixture of polyethers and zwitterionic tensides, for the preparation of a pharmaceutical product which is useful for treatment of caries.

When selecting the suitable treatment composition, in particular when selecting the suitable enzymes for the preparation of a composition for the treatment and removal of caries, one has to consider, for example, which type of caries is present in the particular case.

Generally a difference is made between distinct types of caries. Therefore, for example, caries is classified as broken-down caries with unimpeded access to the dentin, caries lesions wherein carious dentin is still covered with enamel, enamel caries, root caries and root canal caries.

If the spot affected by caries is enclosed with a thick layer of enamel or an old filling and thus is not accessible by the treatment composition, the enamel cover or the old filling may be removed with a fast rotating drill. If, however, the enamel cover is perforated, for example, by an advanced caries disease, it may by penetrated with a composition according to the invention combined with mechanical support without the use of a dental drill. Possible mechanical tools for supporting the penetration of perforated enamel covers comprise a small or micro-brush made of plastics or metal, specimen with a metal tip, specimen with a spoon, specimen with a ball and other tools generally available in a surgery of a dentist for dental use. These tools serve to spread the inventive composition over the site to be treated and to rub said composition in, to remove softened carious dentin and to tactilely make out hard surfaces of dentin and enamel by touch.

If access to the region of the tooth affected by caries is possible, the treatment usually can start with the identification of the carious regions of the tooth in the mouth of the patient. The identification can be carried out by methods known to the dentist, for example by inspection, probing, X-ray, but also by using diagnostic impression materials. The identified, caries infected regions of the tooth are optionally roughly cleaned, for example with a probe or an excavator wherein also abrasion agents may be optionally added. Subsequently the region of the tooth to be treated is rinsed and air-blown. All the described methods are optional in the present case and may not be necessary in order to successfully remove caries according to the present invention.

The caries can be removed by applying the inventive enzyme containing composition onto the carious region of the tooth.

The site to be treated as well as the optionally present cavity can be covered and filled completely with the inventive composition, respectively. A suitable application volume for the treatment of a region of a tooth affected by caries may be, for example, about 100 µl. However, the suitable application volume should be adjusted to the particular case, i.e. the size of the cavity and the size of the region of the tooth affected by caries. Therefore, suitable application volumes can be in the range of from about 0.001 to about 0.5 ml, preferably in the range of from about 0.01 to about 0.3 ml and more preferably in the range of from about 0.02 to about 0.2 ml.

The preferred exposure time of the inventive enzyme containing composition can be in a range of from about 5 s to about 5 min wherein, depending on the size of the caries lesion, the exposure times can be reduced or enhanced. The exposure time is preferably in the range of about 10 s to about 3 min, for example in the range of about 15 s to 2 min or in the range of about 20 s to 1 min.

During the exposure time the carious parts of the caries lesion are degraded, and a larger cavity develops. Once the exposure time has ended, the treated region of the tooth is rinsed and optionally air-blown.

The caries degrading treatment step is carried out, for example, according to the following scheme. A suitable application volume of the enzyme containing composition is applied onto the region of the tooth to be treated, the composition is exposed for about 5 s to about 5 min, and subsequently, the region of the tooth is rinsed with water, for instance. In the following, such a treatment process is referred to as incubation step.

Generally, the incubation step is carried out as often as necessary so that no carious residues remain at the treated region of the tooth. The incubation step can be carried out once or more than once, for example twice or three times or even more often. In most cases, however, it will not be necessary to repeat the incubation step more than twice or three times.

In the context of the present invention it has turned out to be especially advantageous when the incubation step is carried out twice in successive steps. The duration of exposure of the inventive enzyme composition to the region of the tooth affected by caries should be about 10 to about 30 s, for example about 20 s.

Therefore, the present invention also relates to a process of removing caries wherein an inventive composition, in particular an inventive composition comprising at least one solvent is applied to a carious region of a tooth.

Furthermore, the present invention relates to a process of removing caries wherein said process is carried out in two or more incubation steps.

Moreover, the present invention relates to a process of removing caries wherein in a first and in one further or several further steps an inventive composition is applied onto the caries region of a tooth.

A respective acidic treatment composition may provide access to the minerally coated protein parts in a caries lesion via an already porous enamel cover. At the same time the acid removes the mineral structures in the caries lesion. In this way the proteolytic degradation of collagen by the collagenolytic active enzymes is supported. Acid and collagenolytic active enzymes have a synergistic effect in this case.

It can also be advantageous to use an acidic treatment composition which may provide access to the mineral coated protein parts in a caries lesion which additionally contains pepsin. At the same time the acid might remove the mineral structures in the caries lesion and the collagenolytic active enzymes might digest the collagen. This collagenolytic action makes collagen more efficiently digestable for pepsin. In this way the proteolytic degradation of collagen by the collagenolytic active enzymes might be supported by the pepsin. Acid, pepsin and collagenolytic active enzymes might also have a synergistic effect in this case.

In order to prevent the composition described herein from penetrating too deeply into the tooth and thereby also damaging healthy tooth material, use is made of the alkaline property of the hydroxylapatite. The more hydroxylapatite is dissolved, the further the pH value of the composition is shifted towards pH 5.5 which may limit the hydroxyapatite dissolving capacity of the acidic composition containing collagenolytic active enzymes. Therefore, it is assumed that the acidic composition containing collagenolytic active enzymes is not dangerous for healthy regions of the tooth. Furthermore, it is advantageous that the acidic composition containing collagenolytic active enzymes has a germ killing effect.

In the context of the invention, one of the described treatment compositions can be used alone in one or more successive steps for treating caries lesions. According to the invention, however, it is also possible to use the described treatment compositions in combination with each other or in combination with other known compositions or agents for treating caries lesions.

Generally, the sequence of successive treatment steps using an acidic treatment composition and, in addition, other known compositions or agents for treating caries lesions is essentially arbitrary. Thus, the acidic treatment composition and other known compositions or agents for treating caries lesions can be used, for example, in two or more steps alternately or several times in succession one after the other in each case. Thereby, the first treatment step can be carried out with an acidic treatment composition according to the invention or with other known compositions or agents for treating caries lesions.

Preferably a rinsing step takes place between the successive treatment steps wherein the residues of the dissolved parts of the caries lesion are removed together with the residues of the applied compositions.

It can be an effect of the process of treating caries according to the invention that essentially no detectable caries active bacteria remain at the region of the tooth previously affected by caries. This can be proved, for example, by microscopic analyses.

The compositions for the treatment of caries proposed according to the invention can be provided for the end user generally in any facultative form. In the basic form a kit can be provided for the user which comprises at least one of the above mentioned enzymes which then are mixed by the user himself in the necessary amount.

Therefore, the invention also relates to a Kit comprising at least one collagenolytic active enzyme, e.g., a serine-carboxyl proteinase, at least one solvent and at least one acid, wherein said at least one collagenolytic active enzyme, said at least one solvent and said at least one acid are miscible for obtaining a composition according to the invention.

Often it makes sense to combine the treatment using a composition according to the invention with a treatment using another composition known from prior art. In order to facilitate the application for the user also in this case it turned out to be advantageous when said both compositions are provided as a kit as well.

Therefore, the invention also relates to a kit comprising at least one acidic composition according to the invention and at least one composition already known from prior art. When the composition according to the invention is provided in two components, the components can generally be provided in any type of package, e.g., tubes, flasks and the like. For the application of small amounts of liquids, however, the prior art discloses a number of alternatives which facilitate the application of such small amounts of liquid especially in dental applications, where restricted operating space often leads to difficult handling of simple applicators.

According to the invention it is thus preferred, to supply the above mentioned compositions with two components A and B in a technically more advanced package which facilitates mixing and application of the two components. According to the other preferred embodiment of the invention, the two components A and B are supplied in multi chamber applicators as described in WO 02/06820 on pages 3 to 4 and 13 to 17 and FIGS. 1 to 4, DE 100 56 212 A1 column 2 to 10 and FIGS. 1 to 5 and U.S. Pat. No. 6,105,761 column 2 to 5 and FIGS. 1 to 6, respectively. The above mentioned documents are explicitly mentioned and their disclosure, especially the disclosure relating to dispensing devices for multi component compositions disclosed in the above mentioned locations is regarded as being part of the disclosure of the invention.

The invention thus relates to a multi chamber device for storing and dispensing compositions according to the invention, characterized in that at least one chamber contains a collagenolytic active enzyme, e.g., a serine-carboxyl proteinase.

It is preferred according to the invention, if at least one chamber which is not containing a collagenolytic active enzyme contains a substance providing for a pH value at which the collagenolytic active enzyme, after mixing the contents of the chambers, is most active. This substance can be any of the substances mentioned above, which is able to either increase the pH-value (base), lower the pH-value (acid) or form a buffer with a substance in another chamber of the multi chamber device (acid or salt). Respective substances are mentioned in this text.

In another embodiment of the invention a multi chamber device for storing and dispensing liquids is described, wherein at least one chamber contains a component A and at least one chamber contains a component B, wherein component A comprises a collagenolytic active enzyme, e.g., a serine-carboxyl proteinase, preferably Kumamolysin or ScP-A, water, a buffer system providing for a pH value above the pH value at which the composition is most active and a rheological additive and component B comprises water, an acid providing for a pH value of less than or equal to the pH value at which the collagenolytic active enzyme, e.g., the serine-carboxyl proteinase, preferably Kumamolysin or ScP-A, is most active, a thickener and optionally a polyether or a zwitterionic tenside or a mixture of polyethers and zwitterionic tensides.

The invention further relates to the use of at least one collagenolytic active enzyme having its collagenolytic catalytic activity optimum in the acidic pH range of below 7, especially at a pH value of 5.5 at most, for producing a treatment agent for removing caries.

The efficacy of caries removal can be proven by appropriate laboratory methods. These should evaluate the (i) removal of bacteria as the causative agent of caries, (ii) the dentin surface characteristics after completion of the treatment and (iii) quantify the amount of caries removed. The removal of bacteria can be determined by taking a biopsy with a round bur from a tooth before and after treatment as described e. g by Kidd et al. (1993), Br. Dent. J. 174: 245ff. The dentin sample is then homogenated by vortexing together with nutrient broth and glass beads and aliquots are spread on selective nutrient agars for cultivation of total anaerobes, streptococci and lactobacilli. After incubation the number of bacteria before and after treatment as well as the reduction in bacterial count can be determined. The surface characteristics after treatment can be evaluated by fixation of the teeth after treatment followed by evaluation by scanning electron microscopy as described e.g. by Perdigao et al (1995) J Biomed Mat Res 29: 1111ff. The fixation can be done with glutaraldehyde, dehydration can be done in an ethanol series and drying by transfer into hexamethyldisilazane (HMDS) followed by evaporation of HMDS in a fume hood. Afterwards the samples can be carbon sputtered and evaluated by SEM. Caries removal can be quantified by confocal laser scanning microscopy as described e.g. by Banerjee et al (2000) Caries Res 34: 144-150. Here, the difference in autofluorescence between carious and sound dentin can be used to measure the amount of carious dentin removed.

The invention claimed is:

1. A method of caries removal comprising the step of applying a composition to a tooth, said composition comprising:
   one or more collagenolytic active enzymes;
   at least one solvent;
   at least one additive; and
   at least one acid,
   wherein at least one collagenolytic active enzyme is a serine-carboxyl proteinase, and wherein said composition has a collagenolytic activity of more than 5 units per milliliter and a pH value of about 1 to about 5.

2. The method of caries removal according to claim 1 further comprising the step of penetrating tooth enamel by treating a portion of the tooth with a mechanical tool before applying the composition to the treated tooth portion.

3. The method according to claim 1, further comprising the step of removing an existing filling before applying the composition to the tooth.

4. The method according to claim 1, further comprising the step of treating the tooth area affected by caries with a rotating drill before applying the composition to the affected tooth area.

5. The method according to claim 1, wherein the at least one collagenolytic active enzyme is selected from the group consisting of Kumamolysin and ScP-A.

6. The method according to claim 1, wherein the at least one collagenolytic active enzyme is obtainable from *Bacillus novosp.* MN-32 or *Alicyclobacillus sendaiensis* strain NTAP-1.

7. The method according to claim 1, wherein the composition further comprises at least one further proteinase.

8. The method according to claim 7, wherein one of the further proteinases is pepsin.

9. The method according to claim 1, wherein at least one collagenolytic active enzyme is activated by Ca-ions.

10. The method according to claim 1, wherein the at least one additive is selected from the group consisting of thickening agents, rheological additives, polyhydric alcohols, inhibitors, and buffers.

11. The method according to claim 1, further comprising the step of rinsing the region of the tooth to which the composition was applied.

12. A method of caries removal comprising the step of applying a composition to a tooth, said composition comprising:
- at least one collagenolytic active enzyme selected from the group consisting of Kumamolysin and ScP-A;
- at least one solvent;
- at least one additive;
- at least one acid; and
- pepsin,
- wherein said composition has a collagenolytic activity of more than 5 units per milliliter and a pH value of about 1 to about 5.

13. The method of caries removal according to claim 12, further comprising the step of penetrating tooth enamel by treating a portion of the tooth with a mechanical tool before applying the composition to the treated tooth portion.

14. The method according to claim 12, further comprising the step of removing an existing filling before applying the composition to the tooth.

15. The method according to claim 12, further comprising the step of treating the tooth area affected by caries with a rotating drill before applying the composition to the affected tooth area.

16. The method according to claim 12, wherein the at least one collagenolytic active enzyme is obtainable from *Bacillus novosp.* MN-32 or *Alicyclobacillus sendaiensis* strain NTAP-1.

17. The method according to claim 12, wherein the at least one collagenolytic active enzyme is activated by Ca-ions.

18. The method according to claim 12, wherein the at least one additive is selected from the group consisting of thickening agents, rheological additives, polyhydric alcohols, inhibitors, and buffers.

19. The method according to claim 12, further comprising the step of rinsing the region of the tooth to which the composition was applied.

* * * * *

UNITED STATES PATENT AND TRADEMARK OFFICE
CERTIFICATE OF CORRECTION

PATENT NO.        : 8,246,951 B2
APPLICATION NO.   : 12/132315
DATED             : August 21, 2012
INVENTOR(S)       : Oliver Kappler Page 1 of 2

It is certified that error appears in the above-identified patent and that said Letters Patent is hereby corrected as shown below:

Title Page 2, item (56); Column 2 (Other Publications),
Line 3, Delete "pulpo-dential" and insert -- pulpo-dentinal --, therefor.
Line 13, Delete ".widipedia." and insert -- .wikipedia. --, therefor.
Line 15, Delete "microbilolgical" and insert -- microbiological --, therefor.
Line 25, Delete "Bartericidal" and insert -- Bactericidal --, therefor.
Line 29, Delete "Bromphenol" and insert -- Bromophenol --, therefor.

Column 1
Line 35, Delete "whiteish" and insert -- whitish --, therefor.

Column 3
Line 56-57, Delete "-carboxylproteinase," and insert -- -carboxyl proteinase, --, therefor.
Line 61, Delete "-carboxylproteinase" and insert -- -carboxyl proteinase --, therefor.

Column 6
Line 21, Delete "methyethyl" and insert -- methylethyl --, therefor.
Line 22, Delete "methylen" and insert -- methylene --, therefor.

Column 10
Line 14-15, Delete "theological" and insert -- rheological --, therefor.
Line 19, Delete "theological" and insert -- rheological --, therefor.
Line 20, Delete "theological" and insert -- rheological --, therefor.
Line 23, Delete "theological" and insert -- rheological --, therefor.
Line 25, Delete "carragen," and insert -- carrageen, --, therefor.
Line 27, Delete "methycellulose," and insert -- methylcellulose, --, therefor.
Line 29, Delete "theological" and insert -- rheological --, therefor.

Signed and Sealed this
Eighth Day of January, 2013

David J. Kappos
*Director of the United States Patent and Trademark Office*

CERTIFICATE OF CORRECTION (continued)
U.S. Pat. No. 8,246,951 B2

Column 10
Line 52, Delete "theological" and insert -- rheological --, therefor.
Line 54, Delete "theological" and insert -- rheological --, therefor.
Line 62, Delete "(RotorVisco" and insert -- RotoVisco --, therefor.

Column 11
Line 10, Delete "g/1," and insert -- g/l, --, therefor.
Line 12, Delete "g/1." and insert -- g/l. --, therefor.

Column 12
Line 7, Delete "sorbitole," and insert -- sorbitol, --, therefor.

Column 13
Line 30, Delete "(ethylen diamino" and insert -- (ethylene diamine --, therefor.
Line 33, Delete "(ethylen diamino" and insert -- (ethylene diamine --, therefor.
Line 61, Delete "vitamines." and insert -- vitamins. --, therefor.

Column 15
Line 54, Delete "acidicly" and insert -- acidically --, therefor.

Column 16
Line 45, Delete "theological" and insert -- rheological --, therefor.
Line 61, Delete "hydroxid:" and insert -- hydroxide: --, therefor.

Column 18
Line 13, Delete "theological" and insert -- rheological --, therefor.
Line 25, Delete "theological" and insert -- rheological --, therefor.